United States Patent
Bernaz

(10) Patent No.: US 6,497,702 B1
(45) Date of Patent: Dec. 24, 2002

(54) PROBE FOR SKIN HIGH FREQUENCY TREATMENT

(76) Inventor: Gabriel Bernaz, 35 rue Marziano, CH-1227, Carouge (CH)

( * ) Notice: Subject to any disclaimer, the term of this patent is extended or adjusted under 35 U.S.C. 154(b) by 0 days.

(21) Appl. No.: 09/647,511
(22) PCT Filed: Mar. 30, 1999
(86) PCT No.: PCT/IB99/00553
  § 371 (c)(1),
  (2), (4) Date: Sep. 29, 2000
(87) PCT Pub. No.: WO99/49800
  PCT Pub. Date: Oct. 7, 1999

(30) Foreign Application Priority Data

Mar. 30, 1998 (EP) .............................. 98810275

(51) Int. Cl.⁷ ............................................. A61B 18/18
(52) U.S. Cl. ............................... 606/9; 606/10; 606/33; 606/36; 606/43; 607/103
(58) Field of Search ................................. 606/9–10, 33, 606/36, 43; 607/103; 600/9–13

(56) References Cited

U.S. PATENT DOCUMENTS

| | | | | |
|---|---|---|---|---|
| 4,887,614 A | * | 12/1989 | Shirakami et al. | 607/100 |
| 5,090,423 A | * | 2/1992 | Matsuda et al. | 600/10 |
| 5,501,704 A | * | 3/1996 | Chang et al. | 600/26 |

FOREIGN PATENT DOCUMENTS

| | | | | |
|---|---|---|---|---|
| EP | 0 129 607 | | 1/1985 | |
| FR | 2 589 067 | | 4/1987 | |
| FR | 2 680 965 | | 3/1993 | |
| GB | 2 123 287 | | 2/1984 | |
| GB | 2151489 A | * | 1/1985 | A61N/5/00 |
| GB | 2240720 A | * | 8/1991 | A61N/2/02 |
| WO | 89 00027 | | 1/1989 | |
| WO | WO 9304636 A1 | * | 3/1993 | A61B/17/39 |

* cited by examiner

*Primary Examiner*—Lee Cohen
*Assistant Examiner*—H. M. Johnson
(74) *Attorney, Agent, or Firm*—Henderson & Sturm LLP

(57) ABSTRACT

The invention concerns a probe for applying a high frequency electromagnetic energy flux on the skin through a mixture of conductive gel and a treatment product, designed to cause the treatment product to penetrate into the skin. The probe is provided with a non-conductive bearing surface (14), having a plurality of openings (6) around or in the proximity of which inductor elements (5) arranged in successive layers emit an electromagnetic field. The openings (6) emerge through an orifice (3) and contain the gel/treatment product mixture whereof the penetration into the skin is activated by the electromagnetic field. Advantageously, the probe further comprises at least one source of laser electromagnetic radiation (8) arranged inside or aligned with at least one opening (4) emerging in the bearing surface (14), so as to act jointly with the electromagnetic radiation emitted by the inductor element (5).

19 Claims, 5 Drawing Sheets

PROBE FOR SKIN HIGH FREQUENCY TREATMENT

TECHNICAL FIELD

The invention relates to treatment of the skin by high-frequency electric means possibly associated with a source of laser electromagnetic radiation, particularly for so-called "permanent" or "long lasting" depilation, as well as for regrowth of hair.

STATE OF THE ART

WO 93/04636 describes a process based on the observation that by mixing a conductive gel of the usual type used for the application of ultrasound probes to the skin, with a treating product, for example a lotion producing atrophy of the hair roots, it is possible by transcutaneous induction at high-frequency to cause the treating product to penetrate into the follicles (pores) and the hair stems and hence carry out a treatment.

This method hence enables a treatment of the skin to be carried out, notably a cosmetic treatment, for example to achieve long lasting depilation, and which moreover allows a punctual and effective application down to the follicles without a delicate manual intervention.

To carry out the method, WO 93/04636 also describes an apparatus comprising a handleable member for contacting the skin, having a non-conductive body provided with a bearing surface adapted to be applied to the skin. This surface comprises a plurality of discrete conductive electromagnetic emission points for example formed by exposed parts of turns of a solenoid embedded in the body of the contact member. These points are accessible through openings in this surface, and are preferably set back with respect to the latter, so that during use of the apparatus, these points may Contact conductive gel applied to the skin. These discrete emission points emit a high-frequency flux of electromagnetic energy, advantageously a pure emissive current supplied by a high-frequency oscillatory power circuit.

To carry out the same method, WO 96/03928 describes a flexible applicator probe able to conform to the part of the body to which it is applied, comprising non-conductive lower/internal and upper/external parts. At least the lower/internal part is provided with cavities having a plurality of discrete conductive electromagnetic emissive points or areas formed by parts of turns of a coil which are set back in relation to the probe's lower/internal surface.

Another technological approach described in French patent 2 589 067 is a method and apparatus based on the observation that the application to the skin of an electrical field in combination with a laser electromagnetic radiation leads to a modification of the skin's absorption properties.

SUMMARY OF THE INVENTION

The present invention relates to a probe for applying a flux of high-frequency electromagnetic energy to the skin, useful notably in the method described in WO 93/04636 or in French patent 2 589 067, or in any other method necessitating application of a conductive gel, this probe being provided with a non-conductive bearing surface adapted to be applied to the skin, this surface having in its thickness at least one cavity (or opening) that opens out via an orifice into the bearing surface as well as at least one inductor element for inducing an electromagnetic field and arranged to emit an electromagnetic field through said cavity and its orifice.

The probe according to the invention is characterized in that said inductor element is located in its thickness at an intermediate level of the depth of the cavity, this inductor element extending at least partly around and/or being in the proximity of said cavity's wall.

Further characteristics of the probe according to the invention are set out in claims 2–15. The invention also pertains to the use of this probe for cosmetic treatments of the skin, as set out in claims 16–18, and to a method of cosmetic treatment of the skin according to claims 19–23.

When the probe is used, a mixture of gel/active treating product is applied onto the skin to be treated and/or into the cavities of the probe's bearing surface so that this mixture acts as conductive interface between the prober's bearing surface and the skin.

The flexible applicator probe according to the invention has numerous advantages. For instance, the intermediate arrangement of the inductor element for inducing the magnetic field allows this cavity to be enlarged and/or to make it a through-opening traversing the probers thickness, so that a source of a laser beam can be fitted within the probe's thickness or on its upper/outer surface. This arrangement facilitates the simultaneous application of an electromagnetic field and a laser electromagnetic radiation onto the skin, as described in French patent 2 589 067. Moreover, the intermediate arrangement of the magnetic-field inductor element permits easy manufacture of the probes by perforation. Additionally, the arrangement of the magnetic-field inductor elements at least partially around and/or in the proximity of the cavities' wall enables them to be arranged in successive layers, thereby allowing multiplication of the number of the electromagnetic-radiation missive points situated in each cavity. This arrangement furthermore enables the electromagnetic radiation produced by the multiple emission points to act on a greater quantity of the gel/treating product mixture in the cavities. This increases the intensity of the electromagnetic field applied to the gel/treating product mixture and to the skin, hence increasing the treating power of the applied products.

The electromagnetic field inductors are for example made of flattened windings, or of a network or grid of conductive material. The conductive material is preferably a conductive sheet of silicone resin, a fabric of conductive fibers such as carbon fibers, or a non-woven textile made of conductive fibers.

In embodiments comprising a laser electromagnetic radiation source, this source can be constituted either by a laser-emitting diode housed in the thickness of the probe or on its upper face, or by an optical fiber connected to a laser source external to the probe. In these embodiments, one possible arrangement is to arrange the cavities in the support surface in a pattern or along lines forming various geometrical figures, and to position the laser sources in a regular manner in the said pattern or along said lines.

If desired, the applied flux of electromagnetic radiation follow a program determined by the means for generating electrical impulses and the means for exciting the laser sources, for example alternating the two types of electromagnetic radiation and/or varying their intensity.

The probe according to the invention may be used, in combination With a treating gel, for the cosmetic treatment of the skin, in particular long-lasting depilation, baldness, couperosis, varicose veins and capillaries.

BRIEF DESCRIPTION OF THE DRAWINGS

Further features of the invention will be apparent from the following description, given by way of example, with reference to the drawings in which.

DETAILED DESCRIPTION

Figure 1:
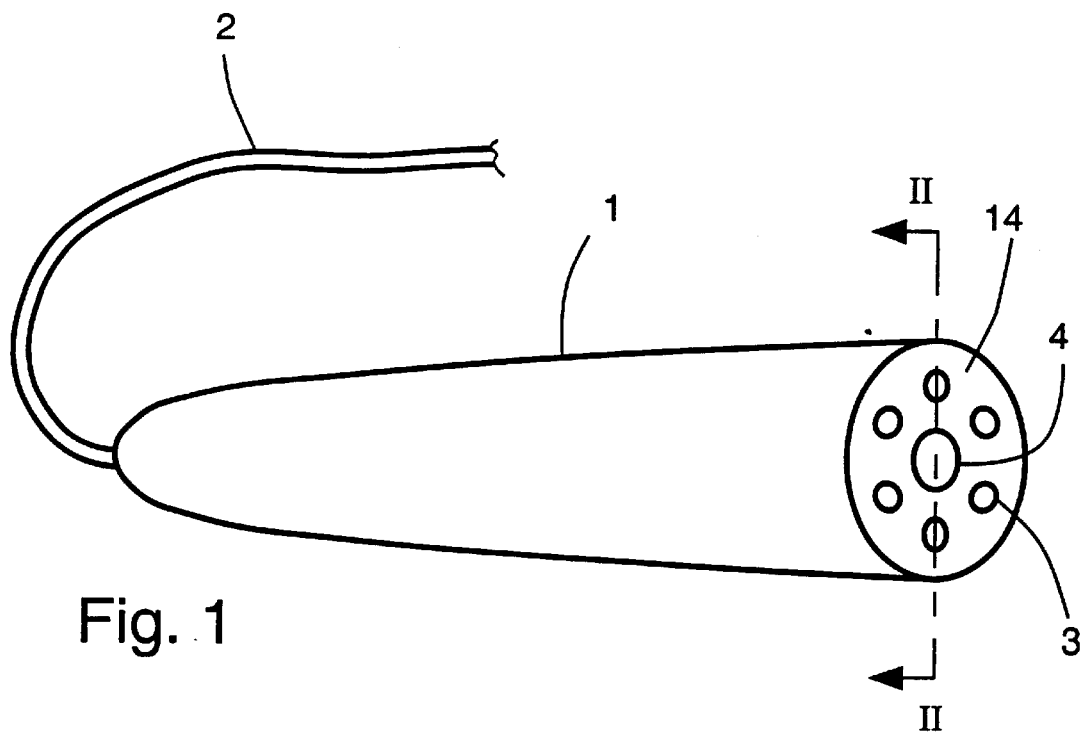
FIG. 1 is a perspective view of a first embodiment of probe according to the invention, made of an elongate handleable member with a laser source.
Figure 2:
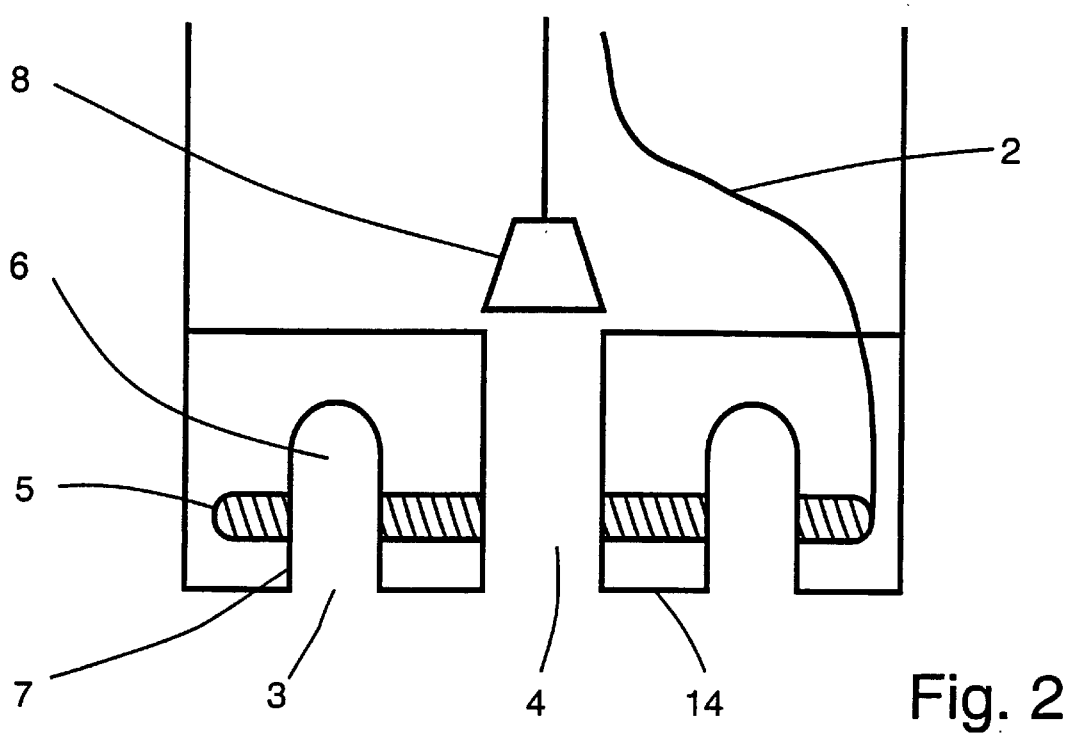
FIG. 2 is a partial view in axial cross-section along line II—II of the probe shown in FIG. 1.

The probe shown in FIGS. 1 and 2 comprises a handleable elongate contact member 1 connected at one of its ends to a current lead 2 and which has at its other end a circular bearing surface 14. The current lead 2 supplies an inductor element 5 for generating an electromagnetic field, recessed relative to the bearing surface, and emitting via several cavities (or openings) 6, namely six of them in this example, which cavities lead into the bearing surface 14. The inductor element 5 for generating the electromagnetic field is situated at an intermediate level in relation to the depth of the cavities 6, this inductor element extending at least partially around and/or in the proximity of the wall 7 of these cavities. A source 8 emits laser electromagnetic radiation though an additional opening 4 situated along the member 1's axis, leading centrally into the bearing surface 14, i.e. centered relative to the cavities 6. The cavities 6 typically have a diameter between 3 mm and 6 mm whereas the opening 4 for the emission of laser radiation typically has a diameter between 6 mm and 10 mm.

Figure 3:
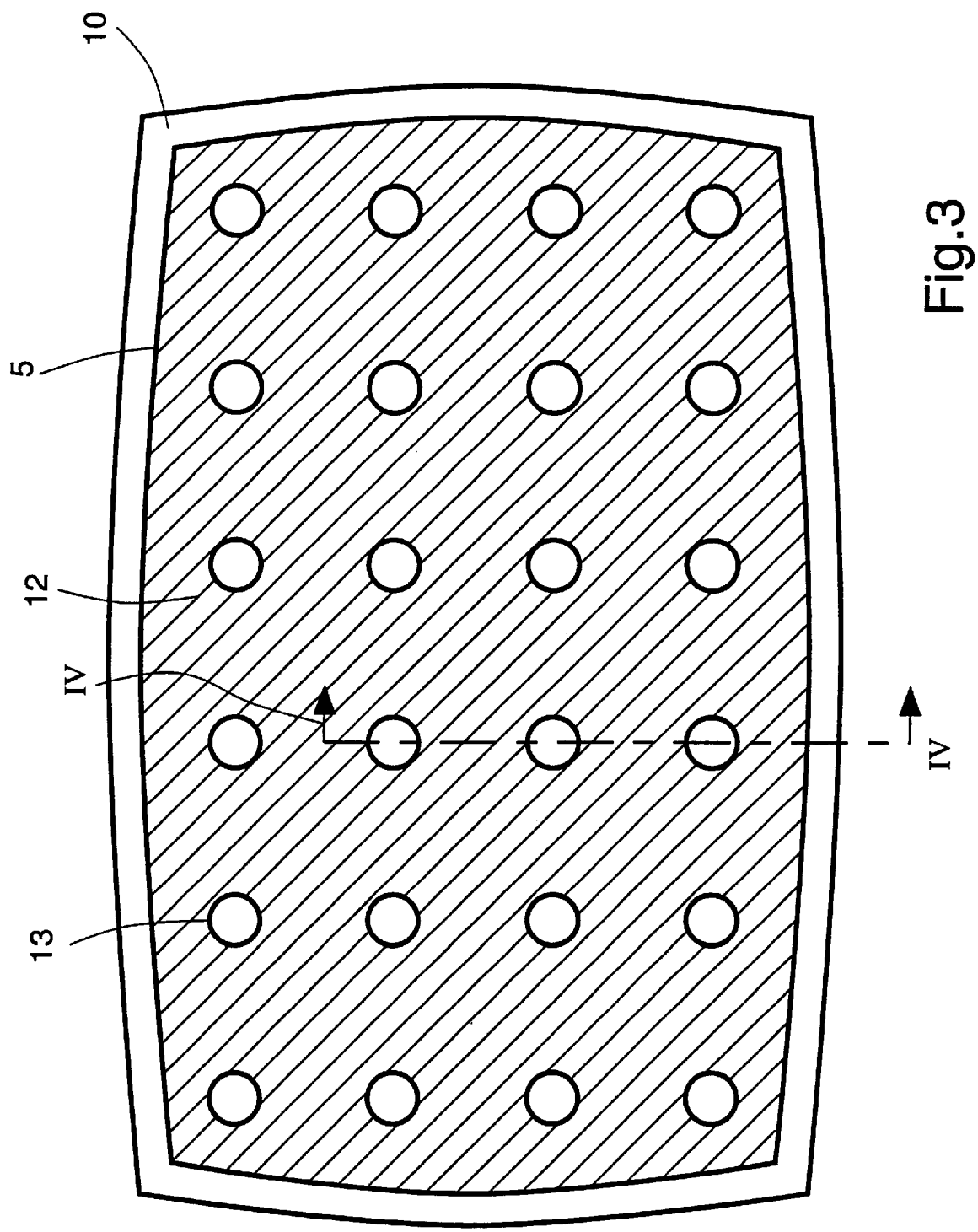
FIG. 3 is a view from below of a sheet forming part of a second embodiment of probe according to the invention.
Figure 4:
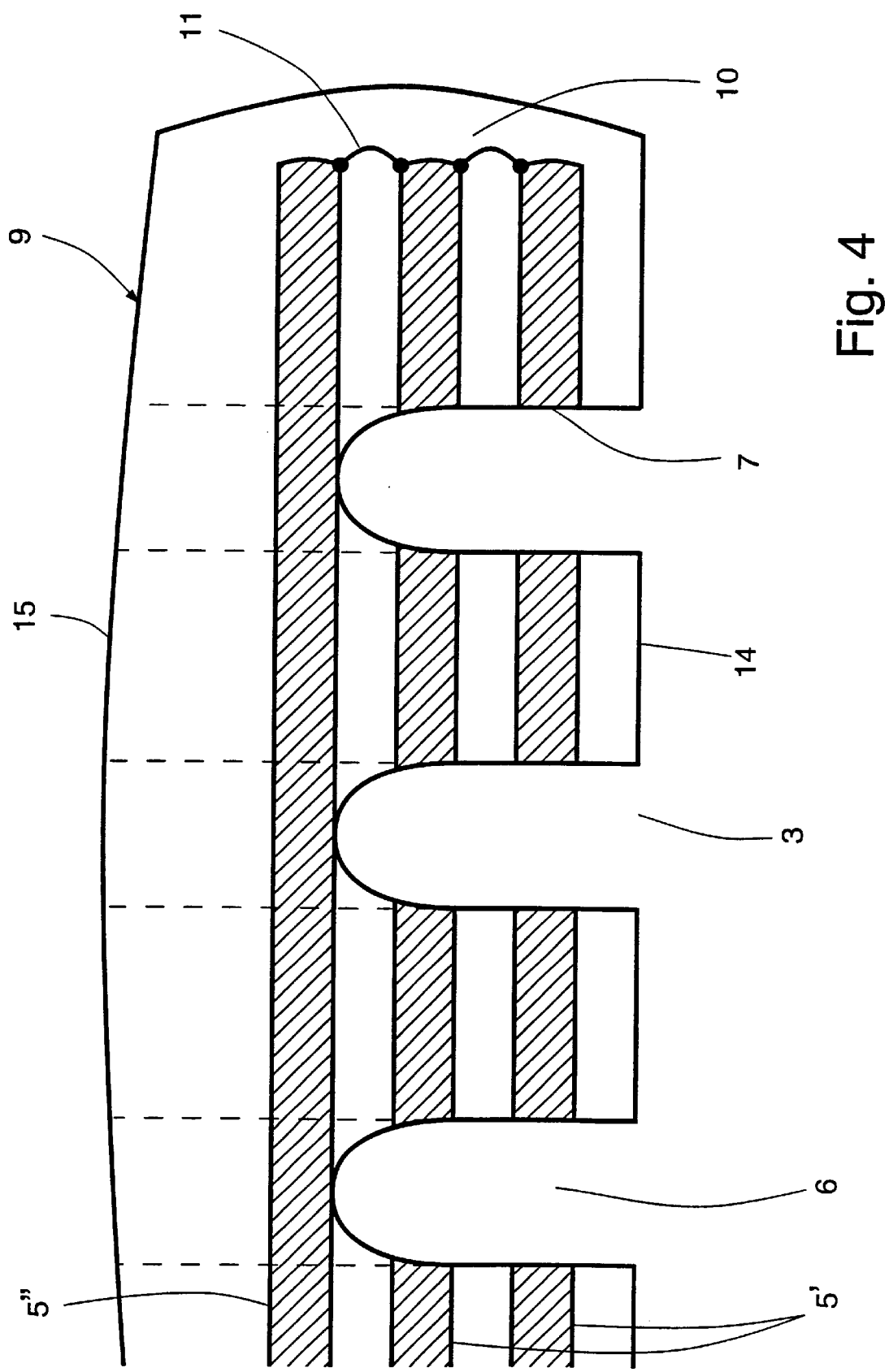
FIG. 4 is a cross-sectional view of a probe including the sheet of FIG. 3, along line IV—IV of FIG. 3.

The embodiment shown in FIGS. 3 and 4 is a flexible probe 9 comprising several (as shown, four) flexible layers of rubber between which are sandwiched several (as shown, three inductor elements 5 occupying the quasi-totality of the flexible probe, except its non-conductive periphery 10. The inductor elements 5 are arranged in several layers electrically connected together by connections 11, and connected to a current lead-in, not shown. FIG. 4 shows two inductor elements 5' situated at intermediate levels of the depth of cavities 6, as well as an optional inductor element 5" situated at the bottom end of the cavities 6. Each inductor element 5 is for example constituted of a woven fabric 12 of carbon fibers having perforations 13. The flexible probe 9 has a lower/inner face constituting the bearing surface 14, and an upper/external face 15. The cavities 6 are situated in the thickness of the sheet of flexible material and open into the lower/inner face 14 by orifices 3. As a modification, shown in dashed lines in FIG. 4, the cavities 6 are perforated through-openings, which simplified manufacture.

Figure 5:
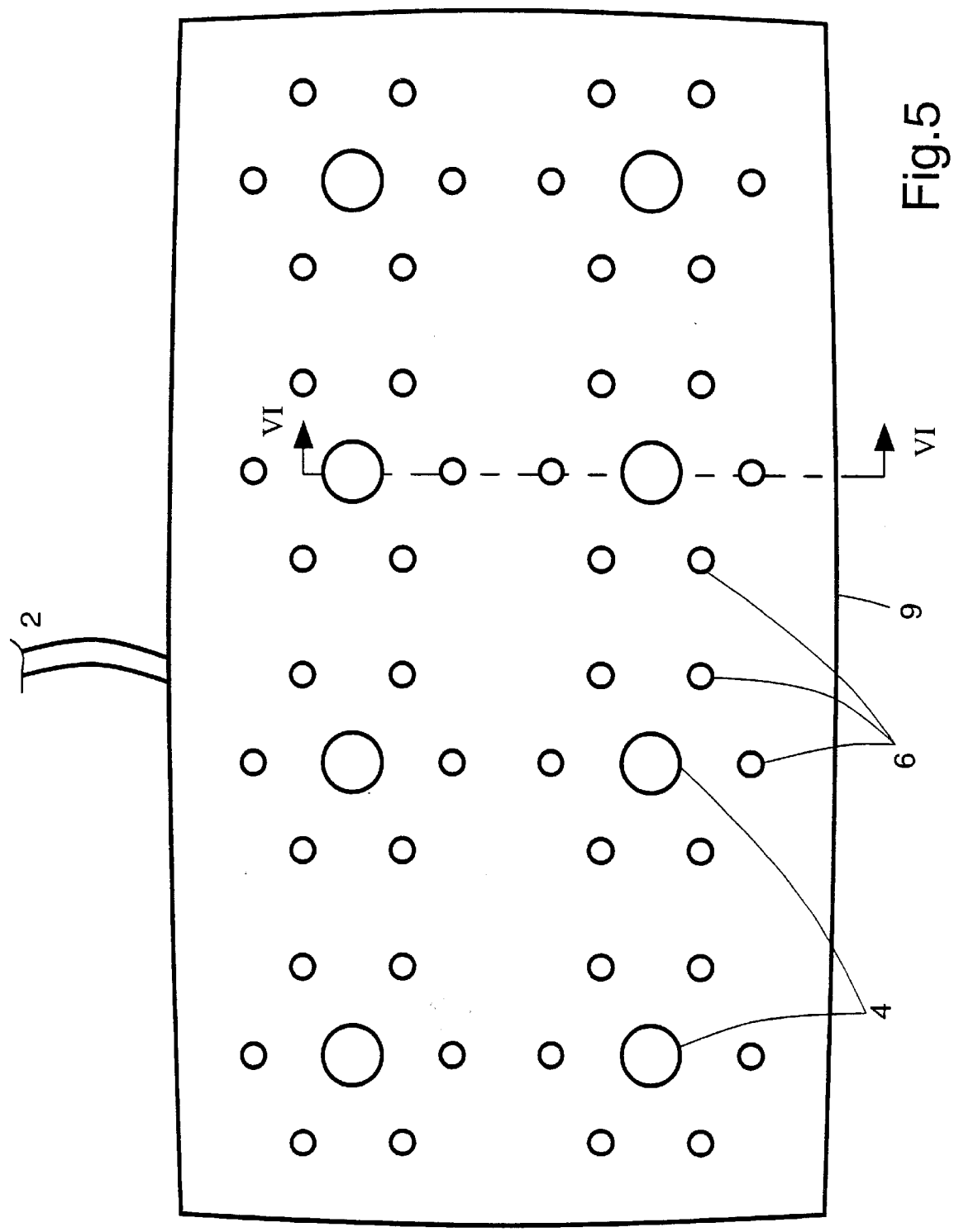
FIG. 5 is a view from below of a third embodiment of probe according to the invention.
Figure 6:
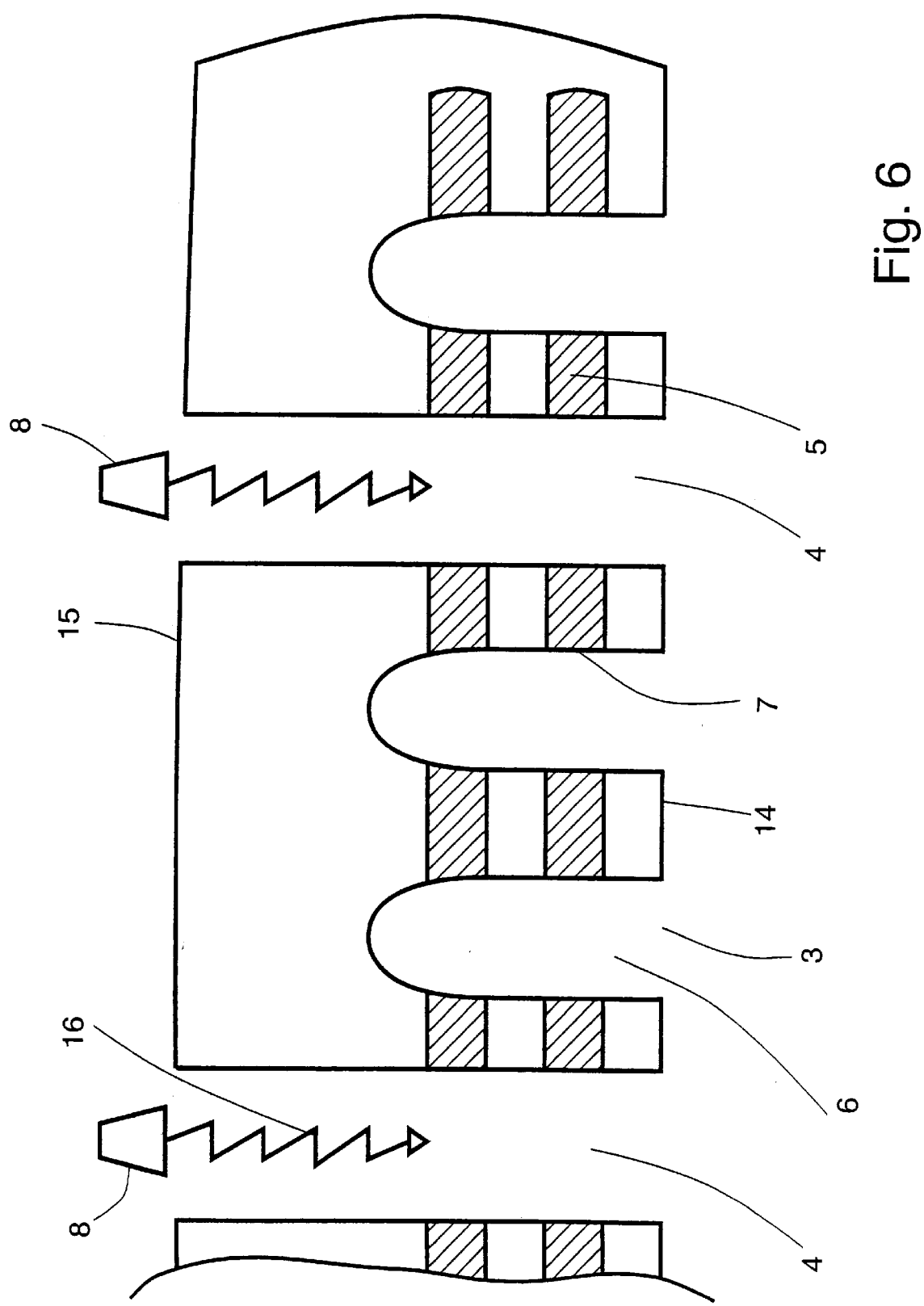
FIG. 6 is a cross-sectional view along line VI—VI of the probe shown in FIG. 5.

The embodiment shown in FIGS. 5 and 6 is a flexible probe 9 comprising laser-emission sources 8. As previously, the probe is in the form of a flexible sheet having a lower/inner face forming the bearing surface 14, and an upper/external face 15. The probe comprises, on the one hand, blind cavities arranged in a repeating pattern forming geometrical figures and, on the other hand, additional through-openings 4 disposed in a regular fashion relative to said pattern, the latter permitting passage of laser electromagnetic radiation 16 emitted by source 8. The cavities 6 are distributed about the through-openings 4 so as to obtain a uniform distribution of the laser radiation. The probe 9 is connected by a current lead 2 to means for generating electrical impulses, connected to the inductor elements 5, as well as to means for exciting the laser sources 8. Examples of these two types of means are described for example in French patent 2 589 067. Furthermore, the laser source advantageously comprises a lens by which the laser beam can be defocalized.

If desired, the different embodiments of probe 9 further include a switch arranged so as to activate the flux of high-frequency electromagnetic energy and excitation of the laser sources when the probe comes into contact with the skin and/or with the gel. This feature increases safety when the probe is used, in particular for embodiments comprising one or more electromagnetic laser sources. This switch, connected to the means for generating electrical pulses and to the means for exciting the laser sources via the current lead 2, can be mechanical, opto-electronic, of the impedance/capacitance type, reacting to the skin and/or to the gel, or of any other type known to the skilled person. As a variation, this switch is connected to a device for timing the switching on or off of the application of the flux of electromagnetic energy when the probe comes into contact with the skin and/or gel, or when it is removed.

Typically, the pulses creating the electromagnetic field are static activation pulses of duration from 1 microsecond to 1 second, And having modulated frequencies with constant ratio from 5 Hz to 1000 Hz. The laser radiation normally has an energy from 0.5 mW to 150 mW. However, higher energies can be used, say 500 mW or more, as long as the beam is defocused by a lens to cover a field of larger surface area.

The loaded gel used for the treatment method is preferably composed of a non-polymerisable conductive gel of a type used usually for coupling ultrasound probes with the skin, mixed with a treating product. The gel has a neutral pH and is for example based on glycol-carboxyvinylic trithanolaminepropylene. The composition of the treating product depends on the desired action. For depilation, one may choose a product providing a progressive atrophy of the hair root, for example a post-depilatory lotion of the type usually used immediately after wax-depilation, as well as during the subsequent days. Such lotions comprise plant extracts, essential oils, demineralised water and possibly other components, for example polyoxyethylenes. These products, known sometimes is "hair regrowth moderators" are non-toxic and generally risk-free when used.

For treating baldness, the gel can be mixed with, for example, minoxydil, or any other product promoting hair regrowth. A mixture of 50:50 volume % of gel and minoxydil has given satisfactory results.

In order not to diminish the conductive properties of the gel, the quantity of active or treating product will in general not exceed 50 weight % of the gel, usually less than 25% (% by weight=, % by volume). Alcohol, sodium chloride and/or other substances may be added to improve the conductivity of the product and/or as conserving agents.

Tests have shown that applying high-frequency energy to the treating product alone or to the gel alone does not produce any special effect, whereas with the mixture a good penetration of the treating product carried by the conductive solution derived from the gel is obtained. It appears that the flow of electromagnetic and electric energy follows the path of least resistance: through the gel and conductive lotion mixture applied to the surface of the skin, and then, around the hair root, only through the conductive lotion which alone penetrates into the follicle and the stem of the hair. The gel allows a progressive release of the active lotion and penetration thereof, under the conjugated action of the electromagnetic and electric fields. In the embodiments having successive layers of inductor elements, the multiplication of the number of points of emission of the electromagnetic field and the cavities amount of the gel/product mixture present in the openings allow a more complete penetration of the treating product. This effect is furthermore reinforced by the adjunction of a laser electromagnetic radiation.

As illustrated in FIGS. 1 and 6, the electromagnetic-field inductor elements 5 also surround the through-openings 4, and form a part of these openings walls. Thus, the gel in these openings 4 is both ionized by the action of the electromagnetic field and traversed by the laser beam, This simultaneous action produces a synergistic affect and promotes a prolonged active duration without danger to the skin.

Advantageously, the probe according to the invention forms part of a set including: one or more rigid probes according to the invention adapted to treat different parts of the body, each rigid probe comprising a laser source (see FIG. 1) or several laser sources arranged in a rigid handleable member, for instance three sources in cavities 4 arranged symmetrically about the member's axis; several flexible probes of different dimensions, with a laser source (for example as in FIGS. 5 and 6) or without a laser source (for example as in FIGS. 3 and 4, or as described in WO 96/03928); and at least one needle fitment for microthemolysis or electrocoagulation. All of these probes and fitments are interchangeable and can be controlled by a central unit, enabling a great variety of different treatments.

What is claimed is:

1. A probe for applying a flux of high-frequency electromagnetic energy to the skin, the probe being provided with a non-conductive bearing surface (14) adapted to be applied to the skin, this surface having in its thickness at least one cavity (6) that opens out via an orifice (3) into the bearing surface as well as at least one inductor element (5,5') for inducing an electromagnetic field and arranged to emit an electromagnetic field through said cavity and its orifice (3);

wherein said inductor element (5,5') is located in said thickness at an intermediate level of the depth of the cavity (6), this inductor element extending at least partly around and/or being in the proximity of said cavity's wall; and wherein said probe comprises at least one source (8) of laser electromagnetic radiation arranged in or aligned with at least one opening (4) leading into the support surface, in such a manner as to act together with the electromagnetic radiation emitted by said inductor element(s) (5, 5').

2. A probe according to claim 1, characterized in that the inductor element(s) (5, 5') is/are constituted of flattened windings.

3. A probe according to claim 1, characterized in that the inductor element(s) is/are constituted of a sheet of conductive material having perforations (13) or cut-outs forming a part of said cavity (6).

4. A probe according to claim 1, characterized in that the inductor element(s) (5,5') is/are constituted of a woven fabric including conductive fibers.

5. A probe according to claim 1, characterized in that the inductor element(s) (5, 5') is/are constituted of a non-woven fabric including conductive fibers.

6. A probe according to claim 1, characterized in that the inductor element(s) (5, 5') is/are constituted of a woven fabric of carbon fibers.

7. A probe according to claim 1, characterized in that at least two inductor element(s) (5') are arranged in discrete layers spaced apart from one another in the thickness of the probe.

8. A probe according to claim 7, having at least one blind cavity (6) leading into the bearing surface (14), characterized in that it further comprises an additional inductor element (5") situated at the bottom of the blind cavity/cavities (6).

9. A probe according to claim 7, characterized in that it is formed of several discrete layers piled as a sandwich and including through-holes (4, 6) produced by perforation.

10. A probe according to claim 1, characterized in that the laser source comprises at least one laser-emitting diode integrated in the probe, or at least one optical fiber connected to at least one laser-emitting device external to the probe.

11. A probe according to claim 1, characterized in that it is in the form of a handleable member (1) for contacting the skin, this member being formed of an elongate body one end of which forms the bearing surface (14).

12. A probe according to claim 1, characterized in that it is in the form of a flexible sheet able to conform to a part of the body against which it is applied, this flexible sheet having a lower/inner face including the bearing surface (14), and a non-conductive upper/external face (15), at least said lower face including said bearing surface (14).

13. A probe according to claim 1, characterized in that cavities (6) leading into the support surface are arranged in a repeating pattern or in alignments forming various geometrical figures, and in that the laser sources (8) are arranged regularly relative to said pattern or lines.

14. A probe according to claim 1, characterized in that it further includes a switch arranged so as to activate the flux of high-frequency electromagnetic energy, and also excitation of the laser source, when the probe comes into contact with skin and/or with the gel.

15. A method for the cosmetic treatment of the skin, using the probe according to claim 1, comprising:

(a) applying to the skin a mixture of conducting gel and a treating product for the cosmetic treatment of the skin;

(b) emitting a high-frequency electromagnetic current from the laser source of the probe into the skin to cause the product to penetrate into the pores of the skin; and (c) applying a laser electromagnetic radiation from the laser source of the probe simultaneously or non-simultaneously to the skin in order to increase the effect of the treating product, its duration of action and its penetration.

16. A method according to claim 15 for long-lasting depilation, characterized by applying to the skin a mixture of conducting gel and a product able to atrophy the hair roots.

17. A method according to claim 15 for the cosmetic treatment of baldness, characterized by applying to the skin a mixture of conducting gel and a hair-regenerating product.

18. A method according to claim 15 for the cosmetic treatment of couperosis, characterized by applying to the skin a Mixture of conducting gel and a product able to atrophy the capillaries.

19. A method according to claim 15 for the cosmetic treatment of varicose vein and capillaries, characterized by applying to the skin a mixture of conducting gel and a product able to atrophy the veins and capillaries.

* * * * *